(12) United States Patent
Schäfer

(10) Patent No.: US 6,301,494 B1
(45) Date of Patent: Oct. 9, 2001

(54) TRANSMITTER FOR COLLECTING HUMAN PULSE BY MEANS OF ELASTIC BANDS

(76) Inventor: Jörg Schäfer, Römerstrasse 18, D-61273, Wehrheim (DE)

( * ) Notice: Subject to any disclaimer, the term of this patent is extended or adjusted under 35 U.S.C. 154(b) by 0 days.

(21) Appl. No.: 09/250,786

(22) Filed: Feb. 16, 1999

(30) Foreign Application Priority Data

Feb. 16, 1998 (DE) .......................................... 298 02 596 U

(51) Int. Cl.⁷ ..................................................... A61B 5/04

(52) U.S. Cl. ............................................................. 600/390
(58) Field of Search ..................................... 600/382, 384, 600/386, 390, 393, 520, 502, 503

(56) References Cited

U.S. PATENT DOCUMENTS

| | | |
|---|---|---|
| 2,096,564 | 10/1937 | Scholl . |
| 4,806,411 | 2/1989 | Mattingly, III et al. . |
| 5,178,163 | 1/1993 | Yewer, Jr. . |
| 5,464,021 | 11/1995 | Birnbaum . |

Primary Examiner—William E. Kamm

(57) ABSTRACT

A transmitter for collecting human pulse by means of flexible bands comprising flexible bands projecting like wings from a transmission unit of a transmitter for human pulse measurement. The flexible bands have contact surfaces of the transmission unit on the inner side and can be stretched around a rib cage by means of a stretch band. To ensure reliable contact and comfortable wearing properties of the flexible bands, the flexible bands have holes each of which widens from the inner side towards the outer of the flexible bands.

8 Claims, 1 Drawing Sheet

TRANSMITTER FOR COLLECTING HUMAN PULSE BY MEANS OF ELASTIC BANDS

BACKGROUND OF THE INVENTION

1. Field of the Invention

The present invention relates to a transmitter for collecting human pulse by means of elastic bands which project from the transmitter like wings, have contact surfaces of a transmission unit on their inside and which, in particular, can be stretched around a rib cage by means of a stretch band.

2. Prior Art

Such transmitters are state-of-the-art devices (e.g., Instructions for Use Phase 4 by the company JS Electronic Sports).

For reliable and accurate pulse measurement in humans, it is important to design the transmitter so as to be comprised of the actual transmission unit and flexible bands connected thereto which project from the transmission unit like wings and have the conductive contact surfaces of the transmission unit on their inside and which, in particular, can be stretched around a rib cage by means of an elastic band. In such a way, it can be ensured that there is good electrical contact between the contact surfaces on the inner side of the flexible bands and the skin of the individual under examination, e.g., beneath the pectora muscles. At the same time, the individual under examination should not feel significantly constrained by the flexible bands nor lose the transmission unit when in motion. Contact can be improved by an additional means, the so-called EKG gel. To achieve this, however. it is necessary to coat the contact surfaces with the EKG gel every time prior to use.

SUMMARY OF THE INVENTION

The present invention deals with the problem to design a transmitter with flexible bands and other characteristics in such a way that reliable contact at the contact surfaces on the inner side of the flexible bands is ensured while a wearing of the transmitter still remains comfortable.

Further, in order to ensure comfort, the transmitter with flexible bands should be as lightweight as possible. According to the present invention, this problem is solved in that the flexible bands have holes which widen from the inner side of the flexible bands towards the outside.

Such design of the holes makes the flexible bands, which can in particular be made of rubber, lightweight while maintaining a relatively large contact surface on the inner side of the bands, at least compared with holes commonly found in perforated wrist watch bands and also in heart rate wrist watch bands, which feature constant clear cross sections throughout the thickness of the bands.

Compared with transmitters with unperforated bands, the transmitter with flexible bands featuring holes as described in the present invention has the additional advantage that the skin can perspire through such holes, which leads to increased wearing comfort.

The flexible bands can be designed particularly light in weight while providing relatively good contact on their inner side, according to which the clear cross sections of the holes widen approximately exponentially from the inner side of the bands towards the outside.

The holes are, therefore, relatively large on the outside and very small on the inner side, thus reducing the contact surface only insignificantly. As a result of the exponential shape of the cross sections, the holes are smooth on the inner side of the bands, which is important for good contact. On the outside of the bands, however, the holes are largely rounded off, resulting in the wearing properties on the outside being additionally improved.

In accordance with the invention, however, such advantageous rounding off is also possible in other, non-exponential types of widening of the free cross sections of the holes.

In a simpler version of widening of the free cross sections of the holes, the holes in the bands widen approximately conically towards the outside.

The holes are further advantageously longitudinally formed in the direction of the flexible band. With this shape, the tension transmission properties of the band are favorable in spite of relatively large holes.

Holes that are distributed approximately evenly over the inner side of the elastic band are also favorable in terms of force transmission and contact.

BRIEF DESCRIPTION OF THE DRAWINGS

One embodiment of the present invention is described below in a drawing with two figures showing important characteristics of the invention.

DETAILED DESCRIPTION OF THE PREFERRED EMBODIMENTS

Figure 1:
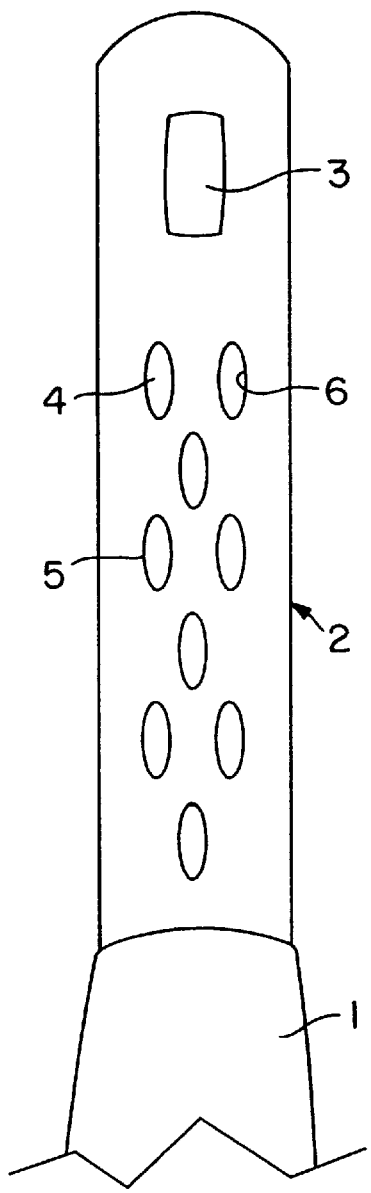
FIG. 1 is a section of the transmitter with a flexible band projecting from one side of the transmission unit, with a similar elastic band projecting from the cutoff side of the transmission uiiit not shown in the drawing.

In FIG. 1, number 1 identifies a part of a transmission unit for heart rate measuring. The transmission unit contains a well-known electronic system with an exchangeable battery as well as a coil transmitting the signals generated by the electronic system and containing the heart rate to a display device not shown herein.

The display device in the form of a wrist watch receives these signals, analyzes them and shows them on a display.

Two flexible bands are located on opposite sides from each other, both projecting from the transmission unit 1 like wings mechanically and are electrically connected with the transmission unit; only one flexible band 2 is shown in FIG. 1. The band is made of rubber, although other materials can be used in other designs.

On one end, the flexible band 2 has a conventionally designed hole 3 for fastening. Between the fastening hole 3 and the transmission unit 1, there are holes which are shown enlarged in the cross section of the flexible band 2 in FIG. 2, of which three holes are shown as 4, 5 and 6. These holes 4, 5 and 6 belong to a group of holes arranged by columns, with the vertical distance between these holes in a column being equal. Horizontally, the holes arranged by columns are also located the same distance from one another. Holes 4 through 6, and the other holes arranged with them, are elongated approximately elliptically in the main direction of the flexible band 2.

Figure 2:
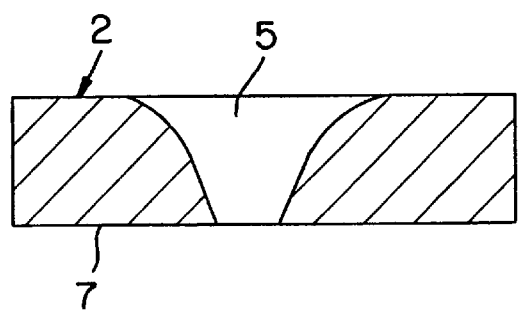
FIG. 2 is an enlarged cross section of the flexible band.

The widening of the cross section of these holes, e.g., of hole 5, is shown in FIG. 2, which represents a cross section through the flexible band 2 in the center of hole 5 perpendicular to above section. The inner side of the flexible band 7, which during use comes in contact with the individual whose heart rate or pulse frequency, respectively, is to be measured, is identified by the number 7 in FIG. 2.

As shown in detail in FIG. 2, hole 5 widens from the inner side 7 towards the outside approximately exponentially in such a way that the hole is small and tightly limited on the inner side 7 while being relatively large and rounded off on the outside, which is not identified by a number.

Figure 3:
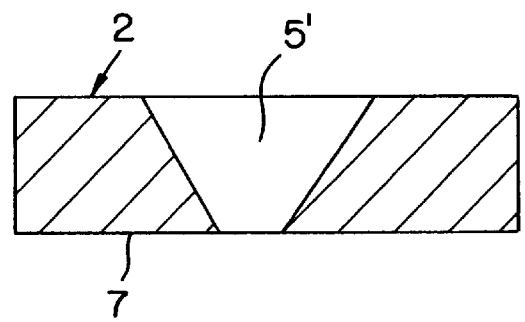
FIG. 3 is an enlarged cross-section of another embodiment of the flexible band of the present invention.

As shown in detail in the embodiment of FIG. 3, the holes 5' widen from the inner side 7 toward the outside approximately conically in such a way that the hole is small and tightly limited on the inner side 7 while being relatively large on the outside.

A transmitter having such flexible bands permits accurate measurement of the heart rate or pulse of a person on its chest while the individual is barely constrained by the flexible bands stretched by an elastic band not shown herein.

What is claimed is:

1. A transmitter for collecting human pulse by means of flexible bands which project like wings from a transmission unit, have conductive contact surfaces of the transmission unit on the inner side and which can be stretched around a rib cage in particular by means of a stretch band, characterized in that the flexible bands have holes which widen from the inner side of the flexible bands towards the outside.

2. A transmitter according to claim 1, characterized in that the holes widen approximately exponentially from the inner side of the bands towards the outside.

3. A transmitter according to claim 1, characterized in that the holes in the bands widen approximately conically towards the outside.

4. A transmitter according to any one of claims 1 through 3, characterized in that the holes are rounded off on the top side of the bands.

5. A transmitter according to claim 4, characterized in that at least two holes are distributed approximately evenly throughout the inner side of the flexible band.

6. A transmitter according to any one of claims 1 through 3, characterized in that the holes are formed longitudinally in the direction of the flexible band.

7. A transmitter according to claim 6, characterized in that at least two holes are distributed approximately evenly throughout the inner side of the flexible band.

8. A transmitter according to any one of claims 1 through 3, characterized in that at least two holes are distributed approximately evenly throughout the inner side of the flexible band.

* * * * *